United States Patent [19]

Neher et al.

[11] 4,041,022
[45] Aug. 9, 1977

[54] PROCESS FOR THE MANUFACTURE OF THYROCALCITONIN

[75] Inventors: Robert Neher, Binningen; Friedrich Werner Kahnt, Basel, both of Switzerland

[73] Assignee: Ciba-Geigy Corporation, Ardsley, N.Y.

[21] Appl. No.: 604,966

[22] Filed: Aug. 15, 1975

Related U.S. Application Data

[63] Continuation of Ser. No. 98,153, Dec. 14, 1970, abandoned, which is a continuation-in-part of Ser. No. 728,897, May 14, 1968, abandoned.

[30] Foreign Application Priority Data

May 24, 1967 Switzerland ............... 7346/67
July 12, 1967 Switzerland ............... 9950/67
Jan. 25, 1968 Switzerland ............... 1159/68

[51] Int. Cl.$^2$ .......................... C07C 103/52
[52] U.S. Cl. ............... 260/112.5 T; 424/177; 424/111
[58] Field of Search ................. 260/112.5 T

[56] References Cited

U.S. PATENT DOCUMENTS 3,590,027  6/1971  Grinnan et al. ............ 260/112

OTHER PUBLICATIONS

Tenenhouse et al.: Proc. Nat. Acad. Sci., 53, 818–821 (1965).
Hawker et al.: Fed. Proc., 26, 392 (1967).

*Primary Examiner*—Delbert R. Phillips
*Attorney, Agent, or Firm*—Joseph G. Kolodny; John J. Maitner; Theodore O. Groeger

[57] ABSTRACT

Pure thyrocalcitonin ($\alpha$ and $\beta$) and process for its manufacture from thyroid gland tissue by extraction with a solvent system containing water and a lower alkanol at a pH of about 1–6.

8 Claims, No Drawings

PROCESS FOR THE MANUFACTURE OF THYROCALCITONIN

CROSS-REFERENCE TO RELATED APPLICATIONS

This is a continuation of application Ser. No. 98,153, filed Dec. 14, 1970, now abandoned, which, inturn, is a continuation-in-part of our application Ser. No. 728,897, filed May 14, 1968, and now abandoned.

The present invention provides an improved process for the manufacture of thyrocalcitonin. The new process is characterized in that degreased thyroid gland tissue, which may first have been extracted with alcohol or aqueous trichloracetic acid, is extracted once or repeatedly with a solvent system containing water and a lower alkanol at a pH value from about 1 to 6, and the resulting solution is worked up in the usual manner, for example as described in Belgian Specification No. 685,991.

The degreased thyroid gland tissue used as starting material is prepared in known manner by extracting thyroid glands of mammals, for example cattle, sheep, goats or especially pigs, with a lipophilic solvent, for example acetone, at a low temperature (see Belgian Specification No. 685,991).

If desired, the resulting powder may be subjected to a preliminary purification with alcohol, for example ethanol of 95 to 96% strength, or with dilute trichloracetic acid, for example with a 15% aqueous solution of trichloracetic acid.

The lower alkanol present in the solvent system is, for example, methanol, ethanol, propanol, n-butanol or secondary butanol. The water content of the system may vary, for example, from 4 to 50% and is preferably from 5 to 30%. The aforementioned acidic pH value is produced for instance with an inorganic acid such as sulfuric or hydrochloric acid, or with an organic acid such as formic or acetic acid, or with an acid buffer such as acetate or citrate buffer. If desired, the solvent system may contain further organic solvents such as acetone or organic bases, for example pyridine or morpholine, and/or inorganic salts such as sodium chloride. Particularly suitable are the systems n-butanol + glacial acetic acid + pyridine + water (17 : 12 : 6 : 15), n-butanol + glacial acetic acid + water (50 : 5 : 14) n-butanol + glacial acetic acid + water (4 : 1 : 5), n-butanol + formic acid + water (50 : 5 : 14), ethanol + 0.05N-hydrochloric acid (70 : 30), ethanol of 80 or 95% strength with dilute hydrochloric acid, acetone + ethanol + dilute hydrochloric acid (3 : 1 : 1).

The degreased and possibly pre-purified thyroid gland tissue is preferably extracted with exclusion of oxygen, for example under nitrogen. (It is advantageous to carry out also the subsequent working-up operations with exclusion of oxygen). The temperature is advantageously kept between 0° and 25° C.

In order to extract the active substance as quantatively as possible with the use of a small quantity of solvent, the extraction may be performed in several stages, using the same or different solvent systems.

After the extraction the residual solid product is removed in any desired manner, for example by filtration with a filter assistant or on the centrifuge. From the solution, which contains practically all the active substance, the latter is obtained in solid form by precipitating the solution with acetone or by lyophilizing or concentrating it and then, if desired, precipitating the active substance from an acid solution with trichloracetic acid. The precipitates thus obtained with acetone or trichloracetic acid may be subjected to one or several extractions with the solvent systems of this invention. For this purpose ethonol of 70% strength at a pH value of about 4 to 6 is a preferred extracting agent. The afore-mentioned extraction and precipitation operations may be combined in any desired way.

The crude product is further purified in the usual manner, for example by lyophilization, partial evaporation, precipitation, dialysis, counter-current distribution, chromatography, ion exchange or electrophoresis.

Dialysis is preferably performed according to the counter-current method. To this end there is used, for example, a "counter-current dialyzer" of which a diagram is shown in FIG. 1.

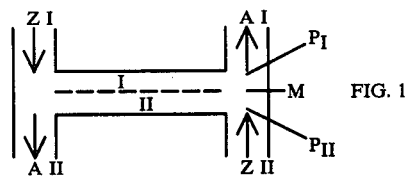

FIG. 1

It consists of two symmetrically fluted plates, $P_I$ and $P_{II}$, made of, for example, plastic material, each ground falt, and tightly screwed together. By means of a membrane M, for example of cellophane, placed between the plates, two circulatory systems, I and II, are created whose exterior connections are built into the plates ($Z_I$ and $A_I$ = inlet and outlet for the solution to be dialyzed; $Z_{II}$ and $A_{II}$ = inlet and outlet for the solvent). The solution to be dialyzed circulates through the system I, while the solvent passes in counter-current direction through the system II. The exchange of substances, for example, dialyzable peptides, salt ions, takes place over the entire length of the circulation path. A number of taps are so arranged as to permit, if desired, the use of but 5/6, 2/3, ⅜, ¼, or ⅛ of the path. The flutes in this device are 5 mm × 1 mm, and their total length is 20 meters (capacity including inlets, 120 ml). The solutions are pumped through the apparatus continuously and by adapting the rate of circulation (and/or shortening the path), also by suitably selecting the membrane, the dialysis can be regulated as required for the particular crude product to be dialyzed, until a sufficiently high degree of fractionation is reached. If desired, the resulting product may be further purified by other means, for example, by Craig distribution or gel-chromatography.

When the purification of the thyrocalcitonin is carried rather far, the substance is split up into various active components, including, among others, α-thyrocalcitonin and β-thyrocalcitonin. When α-thyrocalcitonin is chromatographed on alumina, part of it is split into two components ($α_1$ and $α_2$) which are identical with α-thyrocalcitonin and β-thyrocalcitonin. β-Thyrocalcitonin is the sulfoxide of α-thyrocalcitonin.

The following Examples illustrate the invention.

EXAMPLE 1

A mixture of 10 kg of porcine thyroid gland tissue degreased with acetone and 100 and then 50 liters of solvent system I (= 68 liters n-butanol + 48 liters pyridine + 24 liters glacial acetic acid + 60 liters double distilled water; pH = 5.2) is stirred for 2 hours under nitrogen and then filtered with 1 kg and ½ kg respectively of filter assistant and washed with 25 liters of solvent system I. The combined solutions (175 liters) are cooled to 8° C, while stirring under nitrogen 875 liters of acetone cooled to −20° C are added, and the whole is stirred on for 3 hours. The mixture is then kept overnight at −10° C, the precipitate is filtered off and rinsed with 10 liters of cold acetone. The moist filter residue (2.82 kg; dry content 31.4%) is dissolved by being stirred in 75 liters of 0.025N-hydrochloric acid and cooled to 0° C. Then, within 1 hour, 7.5 kg of solid trichloracetic acid are stirred into the solution, the batch is stirred on for 16 hours at 0° to 5° C, and the precipitate is centrifuged on a percolation centrifuge. The residue on the centrifuge is washed with 2.65 liters of cold 10% trichloracetic acid solution, then washed with 5 × 3 liters of ice-cold acetone and finally with 3 liters of ice-cold ether. After drying at 25° to 30° C, for 48 hours, there are obtained 305 g of a beige-colored product having an activity of 9 MRC-units per gram of acetone dry powder. (The activity was determined according to Kumar et al., J. Endocrin, 33, page 470 [1965]). The product can be purified as described in Example 2.

EXAMPLE 2

103 Grams of degreased porcine thyroid gland tissue (dried with acetone) and 1.5 liters of solvent system II (= 75 liters n-butanol + 7.5 liters glacial acetic acid + 21 liters double distilled water; pH = 2.8) are agitated for 24 hours at room temperature with exclusion of oxygen in an agitating machine. The solid residue is removed on the centrifuge (1 hour, 2500 × g), extracted as described with 750 ml of solvent system II for 5 hours, centrifuged and the residue is once more extracted, this time with 275 ml for 12 hours. The combined solutions (2350 ml) are cooled to 0° C and 12 liters of ice-cold acetone are stirred in. The mixture is stirred on for 1 hour and then kept for 24 hours at −10° C. A faintly pinkish precipitate forms gradually; it is separated by decanting and centrifuging at 0° to 5° C, then washed with 2 × 89 ml of ice-cold acetone and one more centrifuged. The resulting residue is extracted at room temperature with 5 × 50 ml of 0.05N-hydrochloric acid, the extracts are combined and the insoluble matter is removed on the centrifuge. The solution is cooled to 0° C, 24 g of solid trichloracetic acid are stirred in, the whole is stirred for 14 hours at 0° to 5° C, and the fine precipitate is removed on the centrifuge (with about 4500 × g) and washed first with 20 ml of ice-cold 10% trichloracetic acid and then with 4 × 70 ml of ice-cold acetone. While stirring the acetate at room temperature it is extracted with 100 ml of 70% ethanol, the insoluble phase is removed on the centrifuge (with about 4500 × g) and extracted with another 50 ml of 70% ethanol. The two extracts are combined and concentrated in a rotary evaporator to 25 ml under a pressure of about 12 mm Hg. The concentrated solution is cooled to 0° C, 25 ml of ice-cold 25% trichloracetic acid are stirred in dropwise, and the batch is stirred for 18 hours at 0° C with exclusion of air. During this time a fine precipitate gradually forms which is separated on the centrifuge (1 hour; 5000 × g) at 0° to 5° C and washed first with 10 ml of ice-cold 10% trichloracetic acid and then with 4 × 40 ml of ice-cold acetone. The residue is dried under vacuum at room temperature, to yield 400 mg of a light-colored powder. The activity yield is 8 MRC-units per gram of acetone dry powder.

25 Grams of the precipitate obtained as described above are dissolved in 1.5 liters of the bottom phase of solvent system III (= n-butanol + glacial acetic acid + water; 4:1:5, all parts by volume) with addition of 0.5 g of sodium chloride per liter of system with exclusion of oxygen and distributed over the first three tubes of a Craig counter-current current distribution automat. Another 500 ml each of the same bottom phase are introduced into a further 30 tubes, then the apparatus is filled with nitrogen and the distribution process is carried out with 500 ml each of the upper phase per tube over 33 stages. On completion of the distribution aliquote parts of the upper and lower phase are lyophilized and biotested. The most active solutions are found in tubes 25 to 33; they are combined, concentrated to one twentieth of their volume, freed from the precipitate on the centrifuge and 15% by weight of solid trichloracetic acid are added. The whole is kept for several hours at −10 C, then the precipitate is removed on the centrifuge and washed first with 20% trichloracetic acid and then twice with acetone + ether (1:1). While the residue is still moist with acetone it is stirred for 1 hour under nitrogen with about 100 times its own weight of 0.1N-formic acid, treated on the centrifuge, whereupon 1.1 g of insoluble matter separate, and the clear solution is lyophilized. The clear lyophilizate (295 mg) contains 20 MRC-units per mg.

A solution of 20 mg of the above lyophilizate in 2 ml of 0.1N-formic acid is chromatographed on polyacrylamide gel ("Bio-Gel $P_6$") in 0.1N-formic acid. (Column volume 28 ml; fractions of 1.5 ml each; percolation rate 0.1 ml/minute.) The fractions flowing through a registering UV-percolation photometer (254 mm) are tested in animal experiments, then chromatographically (thin-layer chromatography on alumina, silica and Sephadex G-50) and electrophoretically (disc electrophoresis according to Reisfeld et al., Nature 195 page 281 [1962]). The most active fractions contain 1.5 mg of thyrocalcitonin of an activity of 100 MRC-units per mg. The product is subjected to a further Craig distribution over 250 stages in the system n-butanol+N-acetic acid (1:1) with the addition of 250 mg of ammonium acetate per liter of the two phases. Splitting into different active products occurs, mainly α-thyrocalcitonin (distribution coefficient at 20° C, $K^{20}$= 0.82) and β-thyrocalcitonin ($k^{20}$ = 0.25). In the thin-layer chromatogram on alumina (Camag D-O) using the system chloroform + methanol +17% ammonia (41:41:18), β-thyrocalcitonin has an $R_s$ value of 0.85 (S = standard = α-MSH-sulfoxide = 1), whereas α-thyrocalcitonin splits into two active components, $α_1$ and $α_2$; $R_{Sα_1}$= 0.97; $R_{Sα_2}$= 0.88; in system II, the following $R_S$ values were found : $R_{Sβ}$= 1.0; $R_{Sα_1}$= 1.09; $R_{Sα_2}$= 1.0. A similar purification is achieved by a counter-current distribution of this product in a 300-stage Craig apparatus (upper and lower phase 3 ml each) in system III with addition of 0.15 g of sodium chloride per liter of system. The most active fractions are then subjected to gel filtration on Sephadex G or Bio-Gel $P_2$ to free them from their salt content. Thyrocalcitonin purified in this manner displays an activity of 200 MRC-units per mg and is chromatographically and eletrophoretically homogeneous.

EXAMPLE 3

200 Grams of porcine thyroid gland tissue (dried with acetone) are successively extracted with 3000, 1500 and 600 ml of solvent system II (see Example 2), the insoluble phase in each case being removed by centrifuging.

The combined extracts (4.6 liters) furnish on precipitation with 23 liters of ice-cold acetone (as described in Example 2) 37 g of acetone-moist residue, which is extracted first with 500 and then with 250 ml of ethanol of 70% strength with addition of sufficient solvent system IV (= 70 ml of absolute ethanol + 30 ml of 2N-hydrochloric acid) to reach a pH value of 5.0 to 6.0 (measured with a conventional glass electrode). The phase which is insoluble at the pH value mentioned is removed on the centrifuge and the combined extracts (730 ml) are concentrated to 145 ml on a rotary evaporator. On addition of 1.45 ml of 2N-hydrochloric acid the clouding initially formed disappears again. The whole is cooled to 0° C, 14.7 g of solid trichloracetic acid are added to the solution, the precipitate is removed on the centrifuge, rinsed with acetone and dried as in Example 2, to yield 800 mg of a product readily soluble in 0.1N-formic acid, which can be worked up as described in Example 2. The yield of activity is 8 MRC-units per gram of acetone dry powder.

EXAMPLE 4 a. 200 Grams of degreased porcine thyroid gland tissue (dried with acetone) and 2 liters of 70% ethanol are stirred at 20° C under nitrogen and solvent system IV (see Example 3) is dropped in until the pH value, measured with a glass electrode, remains constant at 5.8 for half an hour. Then another 2 liters of 70% ethanol are stirred in, the batch is stirred on for 1½ hours and the insoluble matter is filtered off on a glass suction filter; it is extracted at a pH value of 5.8 to 8.0 first with 1 liter and then with ½ liter of 70% ethanol. The combined extracts are concentrated under vacuum to 1.2 liters in a rotary evaporator and then lyophilized. The lyophilizate is dissolved in 500 ml of 0.02N-hydrochloric acid, filtered through cottonwool, cooled to 0°0 C and precipitated with 50 g of solid trichloracetic acid as described in Example 2. After washing with acetone and drying as described in Example 2, there are obtained 600 mg of a crude product. The yield of activity is 6 MRC-units per gram of acetone dry powder.

b. 80 g of Bio-gel $P_6$ are allowed to swell overnight in 0.1N-formic acid, then filled into a chromatography tube (internal diameter 2.5 cm) up to a height of 94 cm (when it has settled; total volume of the gel bed, 460 ml). 600 mg of the crude product obtained as described under (a) above are dissolved in 20 ml of 0.1N-formic acid, the solution poured on to the gel column, and eluted with 0.1N-formic acid. The eluate is passed through a recording UV percolation photometer (254 nm) and collected in fractions of 15 ml each. The eluates are analyzed by thin-layer chromatography over Sephadex G 25 (superfine) (register Trade Mark) in 0.1N-formic acid (with chlorine/tolidine reagent), and tested biologically. The maximum activity is found in an eluate volume corresponding to 0.8 column volume. The fractions are lyophilized individually and yield 70% of the total activity; the best fractions have an activity of 40 MRC units/mg. The molecular weight of these active substances is below 5000. The product can be further purified by counter-current distribution and/or gel chromatography. For this purpose, batches of 2–5 g of the enriched material are subjected to counter-current distribution over 250–300 stages in the system n-butanol:methanol:0.1N-acetic acid (4:1:5). On biological and chromatograpic checking, 2 active fractions are obtained which have a K-value of about 0.5 and 1.5, respectively. They are subjected to further Bio-gel $P_6$-chromatography in 0.1N-formic acid which brings the specific activity to about 80 MRC units. These fractions still contain trichloracetic acid which, if desired, can be removed by an exchange of ions in 0.1N-acetic or formic acid on "Amberlite" IRA 400 (registered Trade Mark). For further purification, 100–500 mg of the 50–70% product are subjected to counter-current distribution over 800–1100 stages with continuous chromatographic and electrophoretic checking. The systems used are, for example, N-butanol+n-acetic acid (1:1) with 0.25 g of ammonium acetate per liter, or n-butanol+glacial acetic acid+water (4:1:4 to 5:1:4). On repeated lyophilization, chromatographically and electrophoretically unitary α- and β-thyrocalcitonin are obtained each having a specific activity of 200 MRC units per mg of dry substance; the acetate of each of these peptides is readily soluble, whereas the trichloracetate of each is rather sparingly soluble. β-Thyrocalcitonin is stable towards mild oxidation with performic acid, whereas α-thyrocalcitonin becomes a more polar product ($α_2$) which cannot be distinguished from β-thyrocalcitonin by chromatography. Chromatographic comparison of the trypsin degradation products proves that β-thyrocalcitonin differs from α-thyrocalcitonin merely by containing methionine sulfoxide instead of methionine. Trypsin degradation gives three fractions ($Tr_1$, $Tr_2$ and $Tr_3$) which can be separated and isolated in the pure state by counter-current distribution in the ammonium acetate sytem. The fractions are without biological activity. According to aminoacid analysis (see Table 1), a heptapeptide ($Tr_2$), an undecapeptide ($Tr_3$) and a tetradecapeptide ($Tr_1$) are formed. The difference due to methionin/methionine sulfoxide between α- and β-TC makes itself felt in fraction $Tr_3$ only. It follows that α-thyroacalcitonin is a linear dotriacontapeptide having an —S—S— ring. α-Thyrocalcitonin has the formula

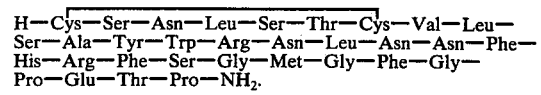

H—Cys—Ser—Asn—Leu—Ser—Thr—Cys—Val—Leu—Ser—Ala—Tyr—Trp—Arg—Asn—Leu—Asn—Asn—Phe—His—Arg—Phe—Ser—Gly—Met—Gly—Phe—Gly—Pro—Glu—Thr—Pro—$NH_2$.

TABLE 1

Analytical data for α-TC and α-TC-sulfoxide (=αλ—TC), and their tryptic fragments.

Table 1

| Analytical data for α-TC and α-TC-sulfoxide (= β-TC), and their tryptic fragments. | | | | | | | |
|---|---|---|---|---|---|---|---|
| | α-TC | α-TC-sulfoxide | α-TC oxidized | $TR_1$ | $Tr_1$ oxidized | $Tr_2$ | $Tr_3$ | $Tr_3$ sulfoxide |
| Trp[1] | 1 | —[2] | 1 | — | 0 | 0 |
| His | 1 | — | 0 | — | 1 | 0 |
| Arg | 2 | — | 1 | — | 1 | 0 |
| Asp/Asn | 4 | 4 | 1 | 1 | 3 | 0 |
| Thr | 2 | 2 | 1 | 1 | 0 | 1 |
| Ser | 4 | 4 | 3 | 3 | 0 | 1 |

Table 1-continued
Analytical data for α-TC and α-TC-sulfoxide (= β-TC), and their tryptic fragments.

|  | α-TC | α-TC-sulfoxide | α-TC oxidized | $TR_1$ | $Tr_1$ oxidized | $Tr_2$ | $Tr_3$ | $Tr_3$ sulfoxide |
|---|---|---|---|---|---|---|---|---|
| Glu/gln | 1 | 1 | 1 | 0 | 0 | 0 |  | 1 |
| Pro | 2 | 2 | 2 | 0 | 0 | 0 |  | 2 |
| Gly | 3 | 3 | 3 | 0 | 0 | 0 |  | 3 |
| Ala | 1 | 1 | 1 | 1 | 1 | 0 |  | 0 |
| 1/2(Cys)2 | 1 | 1.3 | 0 | 1.2 | 0 | 0 |  | 0 |
| Cys(O₃H) | 0 | 0 | 2 | 0 | 2 | 0 |  | 0 |
| Val | 1 | 1 | 1 | 1 | 1 | 0 |  | 0 |
| Met | 1 | 1 | 0 | 0 | 0 | 0 |  | 1 |
| Met(O₂) | 0 | 0 | 1 | 0 | 0 | 0 |  | 0 |
| Leu | 3 | 3 | 3 | 2 | 2 | 1 |  | 0 |
| Tyr | 1 | 1 | 0.5 | 1 | 0.8 | 0 |  | 0 |
| Phe | 3 | 3 | 3 | 0 | 0 | 1 |  | 2 |
| Total amino acids |  | 32 |  | 14 |  | 7 | 11 |  |
| molecular-weight, calculated | 3604 | 3620 |  | 1601 |  | 914 | 1125 | 1141 |
| Thin-layer chromatography[3] |  |  |  |  |  |  |  |  |
| BuOH—AcOH—H₂O (75:7.5:21) | 0.56 | 0.51 |  | 0.53 |  | 0.29 | 0.57 | 0.40 |
| MeOH—CHCl₃—NH₄—OH(41:41:18) | 0:54 | 0.48 |  | 0.51 |  | 0.24 | 0.78 | 0.73 |
| Electrophoresis[4] on cellulose acetate | 1.1 | 1.5 |  | 1.6 |  | 5.3 | 1.6 | 1.9 |
| on Avicel-cellulose |  | 2.9 |  | 2.5 |  | 4.7 | 1.6 |  |

[1] determined by spectrophotometry
[2] — means "not determined"
[3] Rf values on alumina
[4] pH = 1.9; 90 min.; 9 volts/cm. The figures denote cm traveled towards the cathode.

EXAMPLE 5

20 Grams of porcine thyroid gland tissue (dried with acetone) are extracted, as described in Example 2, with the upper phase of the solvent system V (= 75 liters n-butanol + 7.5 liters formic acid = 21 liters double distilled water). Working up of the extract according to Example 4 furnishes a crude product of an activity yield of 7 MRC-units per gram of acetone dry powder.

EXAMPLE 6

500 kg of deep-frozen porcine thyroid glands are minced in a meat cutting machine and introduced into 400 liters of acetone which has first been cooled to −10° C and in which 12 g of sodium ethylene diamine tetraacetate have been dissolved. The resulting magma is stirred into an agitator vessel containing a solution, saturated with nitrogen, of 520 liters of ethanol, 820 liters of acetone, 210 liters of distilled water and 43 liters of concentrated hydrochloric acid. This mixture has a pH of 1.0, as determined by means of a glass electrode; it is stirred under nitrogen for 8 hours at room temperature and then allowed to stand to allow insoluble constituents to settle at the bottom. The supernatant, almost clear, pink-colored solution is suctioned off, and the residue is stirred at room temperature for 4 hours in an atmosphere of nitrogen with 800 liters of a mixture of 160 liters of distilled water, 160 liters of ethanol and 480 liters of acetone. The batch is allowed to stand, the supernatant solution then suctioned off, and the residue centrifuged. The combined solutions (2800 liters) contain the bulk of the thyrocalcitonin (about 75–80%). They are stirred while being slowly treated with concentrated sodium hydroxide solution until the pH constantly remains at 2.9–3.0, as determined with a glass electrode. Under a pressure of 20–40 mm of Hg, and at a bath temperature not exceeding 30° C, the batch is evaporated to half its volume. The concentrate is stirred with 2800 liters of methylene chloride for 1 hour, then allowed to stand for 4 hours. The supernatant, slightly yellow-colored, phase is suctioned off, the methylene chloride phase is washed with 200 liters of 0.02N-hydrochloric acid, and the washing solution combined with the first aqueous phase.

The combined aqueous solutions are completely freed from organic solvents under a pressure of 20–40 mm of Hg at 25° C, concentrated to 700 liters, and cooled to 5° C. The ph is adjusted to 1.5 with 2.7 liters of concentrated hydrochloric acid, and in the course of 2 hours, 84 kg of trichloracetic acid are added portionwise to the solution which is maintained at 0°–5° C. The solution, in which a fine precipitate gradually forms is allowed to stand in the cold for 6 hours. The precipitate is separated from the yellow-colored solution by means of a centrifuge. There are obtained 760 g of a dark-colored, sticky mass which is triturated with 4.5 liters of ice-cold acetone. A sand-colored powder forms in the dark-colored acetone solution. While stirring, 4.5 liters of ether, cooled to −10° C, are added, and the mixture allowed to stand at −10° C. The residue, obtained by centrifuging, is washed twice with cold ether and dried at room temperature under vacuum. The dry powder (335 g) contains 2 MRC units per gram of deep-frozen procine thyroid gland. It can be further purified as described in Example 2.

EXAMPLE 7

A suspension of 40 kg of porcine thyroid gland tissue, defatted with 40 kg of acetone, in 400 liters of absolute ethanol, the pH of which has been adjusted to 6.5 with concentrated HCl, is stirred for 2–3 hours at room temperature. About 360 liters are separated by centrifuging. The preextracted product which still contains about 40 liters of ethanol is introduced into a mixture of 140 liters of ethanol is introduced into a mixture of 140 liters of absolute ethanol and 60 liters of 0.05N-hydrochloric acid; the pH value is lowered from 6.3 to 5.4 by the addition of about 5 liters of a mixture of absolute ethanol and 5 N-hydrochloric acid (7:3), and the batch then stirred for 15 minutes under an atmosphere of nitrogen. 200 liters of 70% ethanol are then added and the batch stirred in an atmosphere of nitrogen for 4 hours at room temperature, the pH being kept at 5.4. By centrifuging, 400 liters of solution are obtained. The residue is extracted for 1 hour with 100 liters of 70% ethanol at ph 5.4. On centrifuging, it yields 100 liters of solution. The two solutions are combined and concentrated in a circulatory evaporator to about one-fifth its volume at a temperature not exceeding 30 ° C. At about 10° C, the alcohol-free, aqueous suspension (90 liters) is adjusted to pH 2 with 5N-hydrochloric acid and freed from the inactive precipitate by centrifuging. The solution obtained by centrifuging and the washing solution obtained by extracting the centrifugate with 10 liters of 0.01N-hydrochloric acid yield 100 liters of a reddish-brown, opalescentcent solution. This solution is cooled to 0°–5° C, treated portionwise with 12 kg of trichloracetic acid, stirred for 12 hours, and allowed to stand at 0°–5° C until a fine precipitate has settled at the bottom. The supernatant solution is separated. The solid residue is a sticky, dark mass; it is triturated with about the 20-fold quantity of cold acetone ($-10°$ C). As soon as a sand-colored powder has formed, the batch is treated with the same volume of ether and allowed to stand at $-10°$ C for several hours. The supernatant solution is removed and the precipitate washed twice at $-10°$ C with a 1:1 mixture of acetone and ether, finally centrifuged, washed with 1 liter of ether, and dried at room temperature under vacuum. Yield: 20 g of a pale powder containing about 6 MRC units/mg. The product can be further purified by gel chromatography as described in Example 4 (b) or by counter-current dialysis as described in Example 8.

EXAMPLE 8

2 g of a crude product obtained as described in Example 4 (a) (0.9 MRC units/mg) are dissolved in 200 ml of 0.1N-formic acid and the solution freed from insoluble matter (169 mg) on a centrifuge (1 hour, 5000 × g). The clear solution has a pH of 2.5. At a rate of 36 ml/h ($v_I$), it is passed through the counter-current dialyzing apparatus (FIG. 1), which has been previously washed with 0.1N-formic acid, against 0.1N-formic acid which is passed through at a rate of 365 ml/h ($v_{II}$). When the entire quantity of the solution to be dialyzed has entered the circulation system I, dialysis is continued with 120 ml (one filling volume) of 0.1N-formic acid ($v_I$= 36 ml/h). From the circulating system II (total, 1090 ml), there are obtained by concentration under reduced pressure in a rotary evaporator and lyophilization of the concentrates, 272 mg of a dark-brown mass which, when dissolved in 0.1N-formic acid to form a 0.1% solution contains at least 3 MRC units/mg.

The solution from the circulating system I (330 ml) is again dialyzed in the same manner against 0.1N-formic acid. The lyophilizate from the system II weighs after this second dialysis 52 mg and is at least as active as the dialyzable portion of the first dialysis. There are thus obtained 324 mg of crude thyrocalcitonin which is free of high-molecular substances; they contain about 50% of the total thyrocalcitonin activity.

EXAMPLE 9

25 g of a product containing 3 MRC units per mg which has been precipitated with trichloracetic acid and prepurified by distribution, are dissolved in 2500 ml of 0.1N-hydrochloric acid. The solution is filtered and, for removal of trichloracetic acid, extracted three times with its own volume of diethyl ether, after having lowered the pH from 3.4 to 2.5 before the last extraction. The hardly colored aqueous phase is freed from ether under reduced pressure, and dialyzed in a counter-current dialyzing apparatus ($v_I$ = 163 ml/h) against doubly distilled water ($v_{II}$ = 365 ml/h).

The solution obtained from circulating system II (4480 ml) is concentrated to 140 ml under reduced pressure and extracted twice with its own volume of diethyl ether. The aqueous phase is freed from ether and lyophilized to obtain 2.95 g of crude thyrocalcitonin (5 MRC units/mg). The solution (2.6 liters) obtained from circulating system I is concentrated under vacuum to 1.5 liters and extracted with 2 × 1 liter of ether. The aqueous phase is freed from ether under vacuum; it then has a pH of 3.2, and is made up to 1500 ml with doubly distilled water, then dialysed ($V_I$ = 121 ml/h) against doubly distilled water ($v_{II}$ = 365 ml/h).

The solution (4530 ml) obtained from circulating system II yields 1.6 g of enriched thyrocalcitonin having 10 MRC units/mg. the solution obtained from circulating system I (1730 ml) is treated with 17.3 of N-formic acid to adjust the pH to 3.4 (previously 4.4 ), and then dialysed against 0.001N-formic acid ($V_I$ = 82 ml/h; $V_{II}$ = 365 ml/h). From 5.3 liters of solution out of circulating system II, another 642 mg of enriched product with an activity of 9 MRC units/mg are obtained.

EXAMPLE 10

A trichloracetic acid precipitate obtained from 450 g of acetone dry powder of porcine thyroid glands according to Example 4 (a) is, without being washed with acetone, agitated in turn with 80 ml and with 40 ml of 0.1N-formic acid and with 10 ml of 0.01N-hydrochloric acid, then centrifuged. The supernatant solutions are combined and made up to 200 ml with 0.01N-formic acid. The solutin which has a pH of 2.4 is dialyzed in a counter-current dialyzing apparatus against 0.01N-formic acid ($V_I$ = 121 ml/h; $V_{II}$ = 365 ml/h). From the circulating system II, 1.1 g of product are obtained which contain about 30% of trichloracetic acid and are biologically inactive. The solution from the circulating system I (360 ml) is made up to 400 ml with 0.01N-formic acid and dialyzed once more against 0.01N-formic acid. ($V_I$ = 121 ml/h; $V_{II}$ = 365 m;/h). From the circulating system II, 213 mg of active product are obtained. Anothe dialysis of the solution, which has first been concentrated to 200 ml, from the circulating system I against 0.01N-formic acid ($v_I$ = 36 ml/h; $v_{II}$ = 365 ml/h) yields 62 mg of purified thyrocalcitonon having 30 MRC/mg. The solution (386 ml) obtained from circulating system I is concentrated under vacuum to 200 ml and again dialysed against 0.01N-formic acid ($v_I$ = 36 ml/h; $v_{II}$ = 365 ml/h). The solution from the circulating system II yields 42 mg of active product, and that from circulating system I 173 mg of product, the latter being substantially less active than the dialyzable portion of the second to fourth dialysis. The new compounds, viz. α-thyrocalcitonin of the formula shown on page 12 and β-thyrocalcitonin which is the met[25]-sulfoxide of α-thyrocalcitonin have a hypocalcaemic effect. They lower the plasma calcium and phosphate contents of the blood of mammals as was demonstrated by tests on Wistar rats. On the perfused isolated shinbone of cats the new compounds produce a diminished calcium resorption. The growth of mouse embryo bones in tissue cultures is increased.

The new compounds act also in humans. On intravenous administration of 0.01 to 1 mg of the compounds dissolved in 0.1 molar acetate buffer at pH 4.6 the serum calcium of hypercalcaemic patients was reduced up to 18 hours by 10 to 20% of the calcium level prior to the treatment. No side effects (temperature, pulse or blood pressure changes) were observed.

In healthy patients the said peptide produces on intravenous, intramuscular or subcutaneous administration a drop in serum calcium by a maximum of 5 to 10%. On the other hand, control patients treated only with buffer solution displayed no change.

The new compounds may therefore be used for treating hypercalcaemia and bone diseases such as osteoporosis.

We claim:

1. Process for the procurement of porcine thyrocalcitonin which comprises extracting defatted porcine thyroid gland tissue at least once with a solvent system comprising essentially water and a lower alkanol at a pH of about 1–6, and precipitating thyrocalcitonin from the extract(s) at least once with trichloracetic acid and subjecting the thus-obtained crude thyrocalcitonin to counter-current distribution in a solvent system containing n-butanol and water and gel chromatography on polyacryl amide having a fractionation range from molecular weights of 1000 – 5000 or to counter-current dialysis to yield the pure (1) thyrocalcitonin, (2) thyrocalcitonin-sulfoxide or (3) mixture of thyrocalcitonin and thyrocalcitonin-sulfoxide.

2. Process according to claim 1, wherein the defatted thyroid gland tissue is pre-purified with 95% ethanol or 15% aqueous trichloracetic acid.

3. Process according to claim 1, wherein a solvent system is used which contains n-butanol as lower alkanol.

4. Process according to claim 1, wherein a solvent system is used which contains ethanol as lower alkanol.

5. Process according to claim 1, wherein a solvent system is used which contains glacial acetic acid.

6. Process according to claim 1, wherein a solvent system is used which contains formic acid.

7. Process according to claim 1, wherein a solvent system is used which contains an organic base, especially pyridine.

8. Process according to claim 1, wherein the resulting crude product is further purified by counter-current dialysis.

* * * * *